US012664008B2

(12) United States Patent House et al.

(10) Patent No.: US 12,664,008 B2
(45) Date of Patent: Jun. 23, 2026

(54) INTERACTIVE USER INTERFACE PORTAL

(71) Applicant: Click to Fill, Inc., Conyers, GA (US)

(72) Inventors: Clint House, Austin, TX (US); Joseph Edward Rector, Gainesville, GA (US); Jeroen Rinzema, Overijssel (NE); Jonathan James Rivera, Wesley Chapel, FL (US); Stuart Robinson, Ratchasima (TH); Samuel Whitten, Tampa, FL (US)

(73) Assignee: Click to Fill, Inc., Conyers, GA (US)

( * ) Notice: Subject to any disclaimer, the term of this patent is extended or adjusted under 35 U.S.C. 154(b) by 0 days.

(21) Appl. No.: 18/649,694

(22) Filed: Apr. 29, 2024

(65) Prior Publication Data

US 2025/0335216 A1     Oct. 30, 2025

(51) Int. Cl.
G06F 9/451          (2018.01)
G16H 40/20          (2018.01)
(52) U.S. Cl.
CPC ............. G06F 9/451 (2018.02); G16H 40/20 (2018.01)
(58) Field of Classification Search
CPC ....................................................... G06F 9/451
USPC ............................ 715/744; 709/201; 717/120
See application file for complete search history.

(56) References Cited

U.S. PATENT DOCUMENTS

2008/0244517 A1* 10/2008 Rostoker ................... G06F 8/10
                                                        717/120
2015/0237115 A1*  8/2015 Kirillov .................. H04L 67/10
                                                        709/201

2016/0162173 A1    6/2016 Chandra
2016/0239881 A1*   8/2016 Bhandari ........... G06Q 30/0247
2016/0266735 A1    9/2016 Törrönen
2017/0337813 A1*  11/2017 Taylor .................. G05D 1/0285
2019/0306258 A1   10/2019 Yamashita et al.
2020/0159888 A1*   5/2020 Ghose ................. G06F 12/0842
2021/0089779 A1*   3/2021 Chan .................... H04N 21/472
2022/0100554 A1*   3/2022 Vityaz .................... G06Q 20/14
2022/0148059 A1*   5/2022 Faricy ................ G06Q 30/0621
2024/0015147 A1    1/2024 Srinivasan et al.

(Continued)

FOREIGN PATENT DOCUMENTS

CN          109257651 A     1/2019
WO    WO-2024097431 A1 *   5/2024

OTHER PUBLICATIONS

International Search Report and Written Opinion, dated Aug. 12, 2025, for PCT Appl. No. PCT/US2025/026785, 9 pages.

*Primary Examiner* — Ruay Ho

(57)          ABSTRACT

Disclosed herein are system, method, and computer program product embodiments for an interactive user interface portal. A specially trained predictive model may detect user interface (e.g., webpage, application, etc.) configurations and recommend a multiple array of entities and services (e.g., healthcare providers/networks, treatment services, etc.). Communication with the entities and services may be facilitated via an interactive portal embedded in the user interface. The entities and services may be identified with respect to user preferences/intent and with consideration of location-based regulations/restrictions. Changes and updates to the user interface may be detected and any services and/or utilities associated with and/or necessitated by the changes and updates may be linked to the interactive portal.

16 Claims, 6 Drawing Sheets

(56)         References Cited

U.S. PATENT DOCUMENTS

2024/0086475 A1 *   3/2024  Chandra  ............. G06F 16/9562
2024/0427999 A1 * 12/2024  Newman  .............. G06F 16/955

* cited by examiner

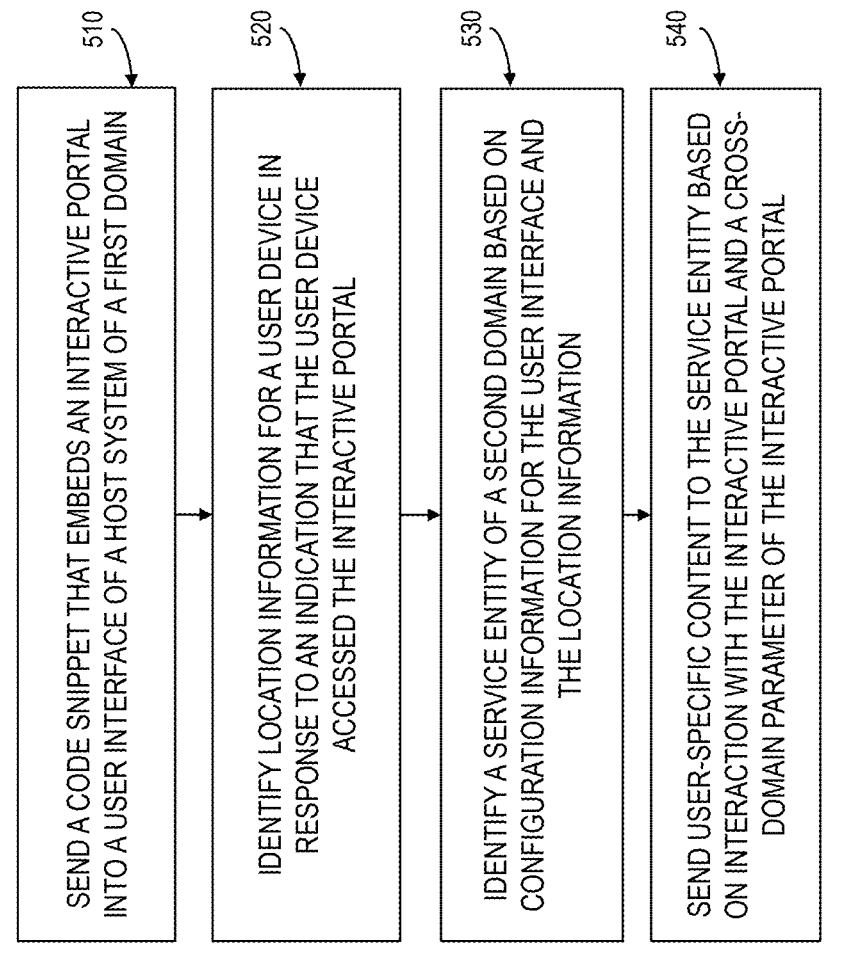

500

510  SEND A CODE SNIPPET THAT EMBEDS AN INTERACTIVE PORTAL INTO A USER INTERFACE OF A HOST SYSTEM OF A FIRST DOMAIN

520  IDENTIFY LOCATION INFORMATION FOR A USER DEVICE IN RESPONSE TO AN INDICATION THAT THE USER DEVICE ACCESSED THE INTERACTIVE PORTAL

530  IDENTIFY A SERVICE ENTITY OF A SECOND DOMAIN BASED ON CONFIGURATION INFORMATION FOR THE USER INTERFACE AND THE LOCATION INFORMATION

540  SEND USER-SPECIFIC CONTENT TO THE SERVICE ENTITY BASED ON INTERACTION WITH THE INTERACTIVE PORTAL AND A CROSS-DOMAIN PARAMETER OF THE INTERACTIVE PORTAL

FIG. 5

INTERACTIVE USER INTERFACE PORTAL

BACKGROUND

Digital healthcare systems use digital technologies to improve the efficiency of healthcare delivery, make medicine more personalized, and give patients more control over their health. As telehealth services become more prevalent, there is a growing need for healthcare providers to seamlessly integrate these services into their existing online platforms. Traditional integration methods often require significant development work, are not easily customizable, and can disrupt the user experience.

BRIEF DESCRIPTION OF THE DRAWINGS

The accompanying drawings are incorporated herein and form a part of the specification.

FIG. 5 shows a flowchart of an example method for an interactive user interface portal, according to some aspects of this disclosure.

In the drawings, like reference numbers generally indicate identical or similar elements. Additionally, generally, the leftmost digit(s) of a reference number identifies the drawing in which the reference number first appears.

DETAILED DESCRIPTION

Figure 1:
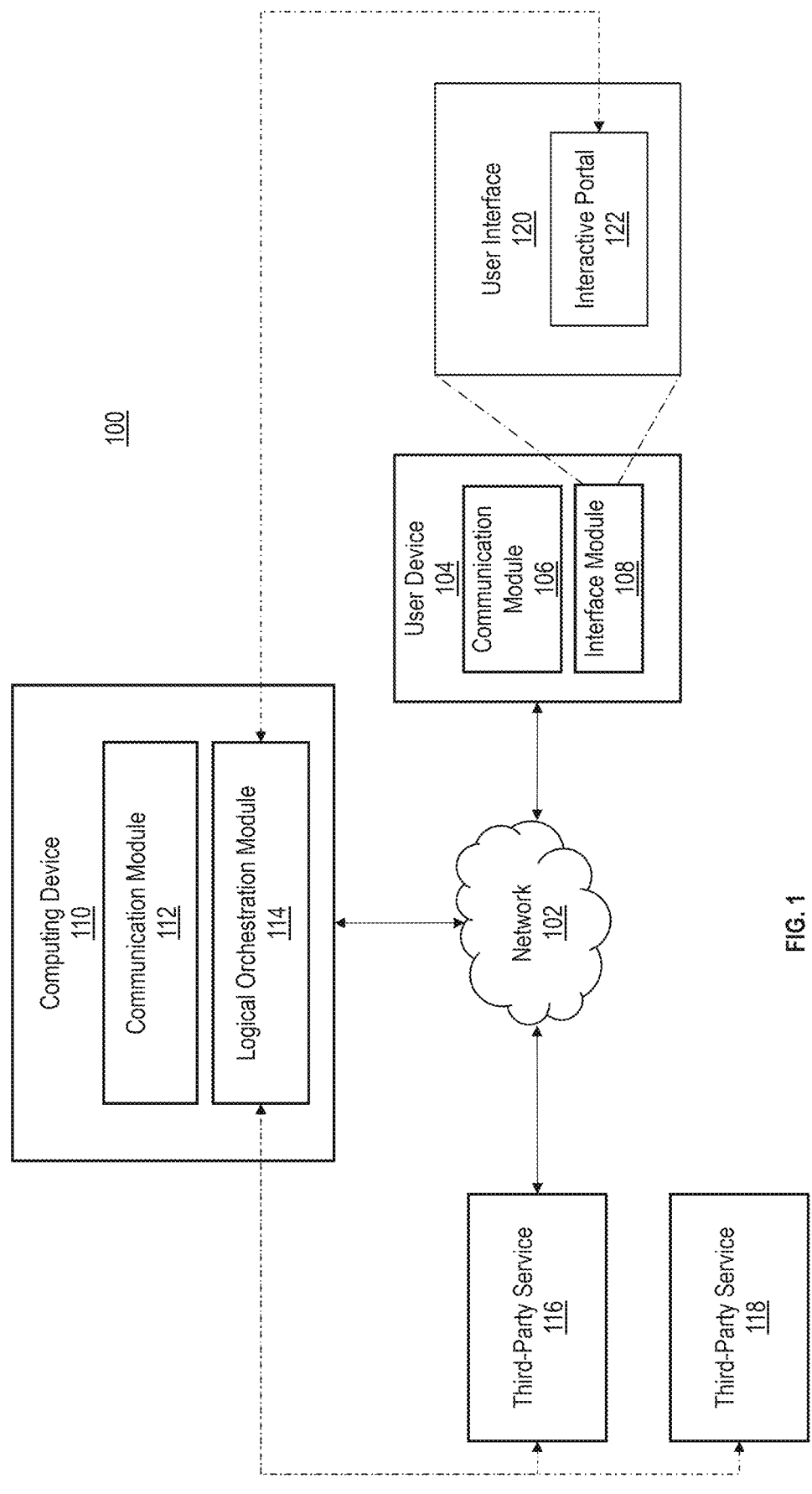
FIG. 1 is a block diagram of a system for an interactive user interface portal, according to some aspects of this disclosure.

Provided herein are system, apparatus, device, method, and/or computer program product embodiments, and/or combinations and sub-combinations thereof, for an interactive user interface portal. Conventional schemes for inter-domain communication between devices and/or entities via a user interface, such as a website, and, application, and the like face several technical challenges including, but not limited to, technology integration complexity, user experience inconsistencies, performance issues, security vulnerabilities, compliance and privacy issues, and/or scalability issues. Conventional schemes for inter-domain communication between devices and/or entities via a user interface routinely involve complex excessive coding, complex back-end integrations with other services or systems, and significant expense of computational resources. This can lead to difficulties in maintaining and updating conventional schemes for inter-domain communication as external services evolve or as the needs and requirements (e.g., design requirements, functionality requirements, service offers/requirements, etc.) for a user interface evolve. Additionally, conventional schemes for inter-domain communication between devices and/or entities via a user interface face challenges with cross-domain communication due to content origin restrictions and other restrictive security practices, which limit the functionality of the user interface for interacting with services hosted on different domains. Further, conventional schemes for embedding content or linking to services via a user interface routinely result in a disjointed user experience, where the look and feel of the embedded content do not match the user interface. The systems, apparatuses, devices, methods, and/or computer program product embodiments (and/or combinations and sub-combinations thereof) described herein enable a seamless exchange of data from multiple disparate third-party data sources through an interactive portal embedded in a common user interface.

For example, an interactive user interface portal may be generated in a host user interface such as a website and/or the like. A specially configured code snippet may be used to embed a white-labeled application programming interface (API) configuration in the host user interface without requiring a change to the existing configuration of the host user interface. As described herein, elements including, but not limited to, a hypertext markup language (HTML) inline frame element, API integration elements, JavaScript-based widgets, reverse proxy arrangements, cross-origin resource sharing (CORS), and/or the like may be used to embed an interactive user interface portal in any user interface.

According to some aspects of this disclosure, when embedded in a user interface, an interactive user interface portal may use event listeners and/or the like to monitor changes/updates to the user interface and automatically enlist necessary services and/or utilities associated with and/or necessitated by the changes. For example, the interactive user interface portal may facilitate the automatic configuration of services (e.g., telehealth services, data services, communication services, etc.) associated with a host user interface, offering a seamless integration that can be customized to match any branding and service offerings of the host user interface.

According to some aspects of this disclosure, when embedded in a user interface, an interactive user interface portal may communicate with a machine learning model trained to detect configurations of the user interface and logically link to and/or recommend a multiple array of entities and services (e.g., healthcare providers/networks, treatment services, etc.) that may be accessed via the interactive user interface portal. According to some aspects of this disclosure, user preferences/intent and location-based regulations/restrictions may be used to dictate which entities and services are linked to the interactive user interface portal. The system, apparatus, device, method, and/or computer program product embodiments for an interactive user interface portal, may use a specially trained predictive model to provide dynamic selection and recommendation of domain-specific services and/or service entities based on deep contextual analysis including, but not limited to, user interface cues, user preferences, legal constraints, and/or the like.

As described herein, an interactive user interface portal empowers user devices and/or entities (e.g., pharmacies, direct-to-consumer companies, labs, large employers, healthcare providers, etc.) to deliver scalable, white-labeled virtual user care-based experiences including, but not limited to remote user monitoring, testing, and diagnostics. The interactive user interface portal can facilitate direct, real-time user-to-user (e.g., patient-physician, etc.) communication across domains and enables flexible analysis of user-based issues via the exchange of content including, but not limited to, questionnaire-based information, biometric information, healthcare-related information, video content, audio content, and the like in a secure manner not supported by conventional systems. The interactive user interface portal may be implemented via a white-labeled configuration to enable host entities and systems to quickly develop and/or update their content (e.g., telehealth-related content, etc.) offerings and outputs with new services or features without the expense of computational resources to develop such capabilities in-house.

As described herein, the system, apparatus, device, method, and/or computer program product embodiments, and/or combinations and sub-combinations thereof, for an interactive user interface portal at least improve the technical fields of digital healthcare, remote care analysis, and/or the like. For example, by implementing an interactive portal (e.g., via an iframe element, etc.) that can dynamically adjust its content based on a user/user device location, browsing history, or preferences, a user experience may customized so that computational resources are not wasted identifying and presenting non-relevant information/services. For instance, users/user devices from different regions could be shown healthcare options and information relevant to their local health regulations and available services. As described herein, code snippets used to implement an interactive portal may also include coding for implementing different security measures that enable the interactive portal to collect and exchange data in real-time, thus providing healthcare providers and related entities insights into user/patient needs, behaviors, and outcomes, and improving remote care analysis by enabling more accurate and timely adjustments to user care plans. Further, the embodiments described herein address the technical challenge of securely accessing data from various third-party sources with different privacy and security settings, all through a single user interface. These and other advantages are described herein.

FIG. 1 shows an example system 100 for an interactive user interface portal. System 100 is merely an example of one suitable system environment and is not intended to suggest any limitation as to the scope of use or functionality of aspects described herein. System 100 should not be interpreted as having any dependency or requirement related to any single module/component or combination of modules/components described therein.

According to some aspects of this disclosure, system 100 may include a network 102. Network 102 may include a packet-switched network (e.g., internet protocol-based network), a non-packet-switched network (e.g., quadrature amplitude modulation-based network), and/or the like. Network 102 may include network adapters, switches, routers, modems, and the like connected through wireless links (e.g., radiofrequency, satellite) and/or physical links (e.g., fiber optic cable, coaxial cable, Ethernet cable, or a combination thereof). Network 102 may include public networks, private networks, wide area networks (e.g., Internet), local area networks, and/or the like. Network 102 may provide and/or support communication from a telephone, cellular phone, modem, and/or other electronic devices to and throughout the system 100. For example, system 100 may include and support communications between a user device 104, a computing device 110, and third-party services 116 and 118 via network 102.

User device 104 may include a smart device, a mobile device, a computing device, and/or any other device capable of communicating with network 102 and/or device/components in communication with network 102. Although only a single user device 104 is shown, according to some aspects of this disclosure, system 100 may include any number of user devices 104.

User device 104 may include a communication module 106 that facilitates and/or enables communication with network 102 (e.g., devices, components, and/or systems of network 102, etc.), computing device 110, third-party services 116 and 118, and/or any other device/component of the system 100. For example, communication module 106 may include hardware and/or software to facilitate communication. Communication module 106 may comprise one or more of a modem, transceiver (e.g., wireless transceiver, etc.), digital-to-analog converter, analog-to-digital converter, encoder, decoder, modulator, demodulator, tuner (e.g., quadrature amplitude modulation (QAM) tuner, quadrature phase shift keying (QPSK) tuner), and/or the like. Communication module 106 may include any hardware and/or software necessary to facilitate communication.

According to some aspects of this disclosure, user device 104 may include an interface module 108. Interface module 108 enables a user to interact with user device 104, network 102, computing device 110, third-party services 116 and 118, and/or any other device/component of system 100. Interface module 108 may include one or more input/output devices and/or components, for example, such as a display, a keyboard, a pointing device (e.g., a computer mouse, remote control), a microphone, a camera, a joystick, a tactile input device (e.g., touch screen, gloves, etc.), and/or the like. According to some aspects of this disclosure, interaction with the input/output devices and/or components may enable a user to view, access, interact, request, and/or navigate a user interface generated, accessible, and/or displayed by interface module 108. According to some aspects of this disclosure, interaction with the input devices and/or components may enable a user to manipulate and/or interact with components of a user interface, for example, such as an interactive user interface portal and/or the like.

Interface module 108 may include any interface for presenting and/or receiving information to/from a user. According to some aspects of this disclosure, interface module 108 may include a user interface 120. User interface 120 may be and/or may include a web browser, a website, an application, and the like. Other software, hardware, and/or interfaces can be used to provide communication between user device 104, network 102, computing device 110, third-party services 116 and 118, and/or any other device/component of system 100. User interface 120 may request/query and/or send/provide various files from a local source and/or a remote source, such as computing device 110, third-party services 116 and 118, and/or any other device/component of system 100.

User interface 120 may be supported and/or provided by a host system (not shown). According to some aspects of this disclosure, a host system may include software and/or hardware that uses communication protocols including, but not limited to HTTP (Hypertext Transfer Protocol) and/or the like to respond to requests from user device 104. The host system may respond to requests from user device 104 with data/information needed to generate, render, cause user interface 120 to be displayed, and/or cause at least components of user interface 120 to be in communication with (or accessible by) user device 104.

For example, user device 104 may display user interface 120 by processing information including, but not limited to, a markup language document received from the host system using a browser application of interface module 108. For example, a markup language document may identify content and configuration information (e.g., one or more instructions, etc.) describing formatting and/or presentation of content within user interface 120. By executing the configuration information included in the markup language document, interface module 108 displays the content using the format and/or presentation described by the markup language document. For example, the markup language document may include configurations/instructions for generating and displaying a web page having multiple frames that include text and/or image data retrieved from the host system.

According to some aspects of this disclosure, the markup language document may include a data file including extensible markup language (XML) data, extensible hypertext markup language (XHTML) data, or other markup language data. Additionally, a markup language document may include JavaScript Object Notation (JSON) data, JSON with padding (JSONP), and JavaScript data to facilitate lightweight data interchange between the host system and user device 104. Interface module 108 may include a compiler such as a JavaScript compiler and/or the like to decode the markup language document.

According to some aspects of this disclosure, computing device 110 may include a server, a cloud-based compute resource, an entity-controlled device, or any other device capable of communicating with user device 104, third-party services 116 and 118, and/or any other device/component of system 100, either described or (un) shown. Although shown as a single device, according to some aspects of this disclosure, computing device 110 may be part of a computing system and/or infrastructure, and/or may represent a plurality of computing devices. For example, computing device 110 may represent a plurality of computing devices in communication with user device 104, third-party services 116 and 118, and/or any other device/component of system 100.

According to some aspects of this disclosure, computing device 110 may include communication module 112 that facilitates and/or enables communication with network 102 (e.g., devices, components, and/or systems of network 102, etc.), user device 104, third-party services 116 and 118, and/or any other device/component of system 100. For example, communication module 112 may include hardware and/or software to facilitate communication. According to some aspects of this disclosure, communication module 112 may include one or more of a modem, transceiver (e.g., wireless transceiver, etc.), digital-to-analog converter, analog-to-digital converter, encoder, decoder, modulator, demodulator, tuner (e.g., QAM tuner, QPSK tuner), and/or the like. According to some aspects of this disclosure, communication module 112 may include any hardware and/or software necessary to facilitate communication.

According to some aspects of this disclosure, computing device 110 may include software and/or hardware that uses communication protocols including, but not limited to HTTP (Hypertext Transfer Protocol) and/or the like to respond to requests from user device 104. Computing device 110 may respond to requests from user device 104 with data/information needed to generate, render, and/or cause to be displayed an interactive portal within a user interface associated with a host entity/domain and displayed by user device 104.

Computing device 110 may include and/or be configured with a representational state transfer (REST) API that facilitates interactions with RESTful services, such as interactive elements (e.g., pop-ups, selectable items, informational items, etc.) and/or the like. According to some aspects of this disclosure, displaying, rendering, and/or presenting interactive elements may be facilitated via a just-in-time compiled programming language such as JavaScript, Typescript, Dart, ClojureScript, Ruby, Python, and/or the like. Additionally, technology including JavaScript with dynamic generation of a Document Object Model (DOM), Cascading Style Sheets (CSS), jQuery, Asynchronous JavaScript and XML (AJAX), and code libraries may be used to generate, render, and/or cause the display of one or more interactive elements within user interface 120.

According to some aspects of this disclosure, user interface 120 may be associated with a host system (e.g., a server hosting a website, a cloud-based service supporting/providing a user interface, a device/system supporting/enabling an application, etc.) and/or a domain (e.g. an Internet domain, a website, an application, etc.). For example, user interface 120 may be a website/webpage hosted and/or maintained by a host entity. User interface 120 may include an interactive portal 122. According to some aspects of this disclosure, interactive portal 122 may be implemented via a white-labeled API configuration that utilizes an HTML iframe and/or the like to embed interactive portal 122 in user interface 120 without requiring a change to the existing configuration of user interface 120.

For example, to implement interactive portal 122 a host domain that supports and/or provides user interface 120 may send a request to computing device 110 for access to a portal that provides one or more services including, but not limited to, healthcare-related services and/or the like. Computing device 110 may send user interface 120 code snippets that embed interactive portal 122 in user interface 120. The code snippet may include code for implementing a hypertext markup language (HTML) inline frame element, an API integration, JavaScript-based widgets, reverse proxy configurations, cross-origin resource sharing (CORS) configurations, and/or the like. For example, the code snippet may include a HTML iframe element that causes interactive portal 122 to display content within user interface 120.

According to some aspects of this disclosure, a host system and/or a particular domain supporting user interface 120 may incorporate the code snippet into user interface 120 without requiring modifications to the existing configuration of user interface 120. The HTML iframe element may be configured to adapt any content displayed by user interface 120 to match the visual design elements of the host system. For example, by configuring interactive portal 122 with user interface 120 under a white-labeled arrangement, interactive portal 122 may be visually and functionally integrated into user interface 120 as if it were a native component of user interface 120.

Figure 2:
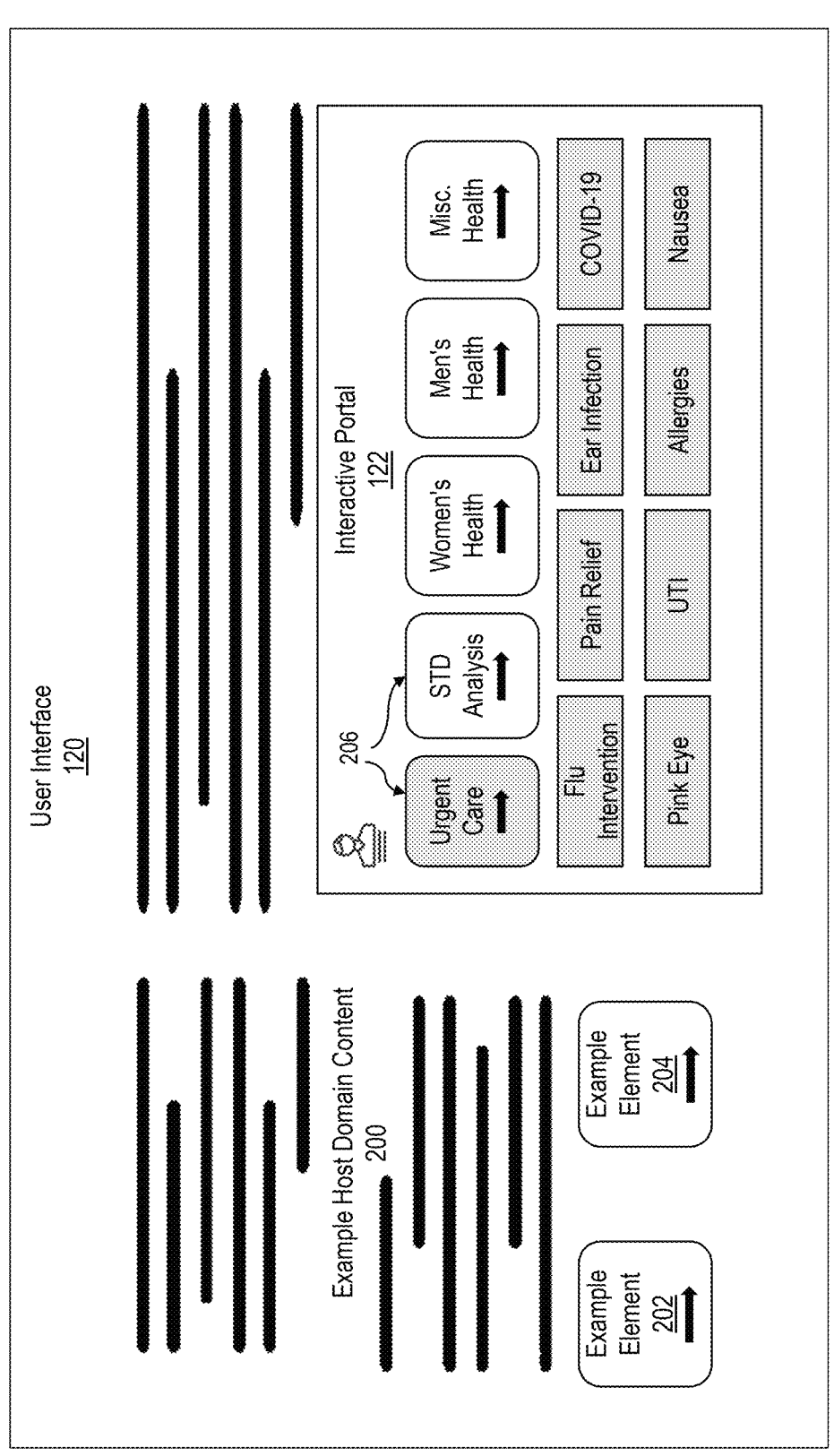
FIG. 2 shows an example user interface embedded with an interactive user interface portal, according to some aspects of this disclosure.

FIG. 2 shows an example of user interface 120. As shown, user interface 120 may include example host domain content. For example, user interface 120 may be a website/webpage hosted by a merchant and the example host domain content 200 may include information related to merchant offerings, products, services, and/or the like. The example host domain content may include any content and/or information. User interface 120 may also include interactive user interface elements (e.g., icons, links, selectable items, emoji, etc.) such as example elements 202 and 204. As previously described, interactive portal 122 may be configured with user interface 120 such that interactive portal 122 may be visually and functionally integrated into user interface 120 as if it were a native component of user interface 120. As shown, interactive portal 122 may include interactive user interface elements (e.g., icons, links, selectable items, emoji, etc.) such as interactive elements 206 that are visually similar (e.g., similar shape, similar color, similar font, etc.) and functionally similar (e.g., hyperlink-enabled, selectable, etc.) to example elements 202 and 204. For example, interactive elements 206 and example elements 202 and 204 may each be selectable/interactive elements, that when selected/interacted, enable a user/user device to link to additional information and/or communicate with another user, party, and/or user device.

Interactive portal 122 may be visually and functionally integrated into user interface 120 as if it were a native component of user interface 120 by identifying visual design elements (e.g., borders, fonts, color, etc.) of user interface 120 and adjusting visual design parameters of interactive portal 122 so that the visual design elements of interactive portal 122 match the visual design elements of user interface 120. For example, a customer script may be run by computing device 110 to fetch and analyze user interface 120 for specific design elements. The script may enable a combination of HTML and cascading style sheets (CSS) parsing to identify visual design elements of user interface 120. According to some aspects of this disclosure, visual design elements of user interface 120 may be identified by computing device 1110 sending user interface 120 an instruction that causes user interface 120 to transition to a headless mode where computing device 110 may be enabled full access to rendering and JavaScript execution capabilities of user interface 120. Any visual design parameters of interactive portal 122 may be automatically set, modified, adjusted, updated, and/or the like to match the visual design elements of user interface 120.

Interactive portal 122 may include interactive functionality. For example, interactive portal 122 enables user-specific content to be communicated between user device 104 and third-party services 116 and 118. Interactive portal 122 may facilitate telehealth services, remote patient monitoring, and/or the like based on interaction with interactive elements (e.g., interactive elements 206, etc.) of interactive portal 122. For example, interactive portal 122 enables a user and/or user device 104 to communicate user-specific data such as biometric information, healthcare-related information, questionnaire-based information, video content, audio content, and/or the like to one or more services and/or entities (e.g., third-party services 116 and 118, etc.). Interactive portal 122 enables a user and/or user device 104 to communicate any data such to one or more services and/or entities linked to and/or in communication with interactive portal 122.

Returning to FIG. 1, when interactive portal 122 is integrated/incorporated into user interface 120, interactive portal 122 may be used to communicate data including, but not limited to, user interactions with interactive portal 122, health-related information, and/or the like. A secure communication channel may be established between interactive portal 122 and the host system/domain of user interface 120. A cross-origin resource sharing (CORS) policy may be implemented for user interface 120 and interactive portal 122 to restrict the resources to be accessed by the embedded portal, limiting interactions to trusted domains (e.g., third-party services 116 and 118, etc.).

A secure channel between interactive portal 122 and the host system/domain of user interface 120 may employ a variety of encryption schemes/techniques to ensure data privacy and compliance with applicable health information privacy regulations. Interactive portal 122 enables users/user device 104 to communicate with third-party services 116 and 118 without departing from user interface 120 of the host system/domain. For example, a modification of an iframe element (or equivalent) may be used to facilitate cross-domain communication between a host system/do-main for user interface 120 and respective domains for third-party services 116 and 118.

For example, to facilitate cross-domain communication between a host system/domain for user interface 120 and respective domains for third-party services 116 and 118, a URL indicated by an iframe supporting interactive portal 122 may be manipulated by computing device 110. Computing device 110 may send an instruction via an application and/or the like that manipulates an iframe supporting interactive portal 122 by updating a URL associated with a listener of the iframe and includes, in the URL, any message that is desired to be communicated to the iframe. Additionally, computing device 110 may send an instruction via an application and/or the like that manipulates a parameter such as a header control parameter (e.g., 'Access-Control-Allow-Origin', etc.) used in exchange messages, a sandbox parameter (e.g., 'sandbox', etc.), a script-enabling parameter (e.g., 'allow-scripts', etc.) that allows the iframe to execute scripts, a form-enabling parameter (e.g., 'allow-forms', etc.) that allows form submission from the iframe to other domains, a message-enabling parameter (e.g., 'postMessage', etc.) to enable a message to be sent between interactive portal 122 and a target, and/or the like. Computing device 110 may send an instruction that manipulates (or causes to be manipulated) any parameter associated with interactive portal 122.

According to some aspects of this disclosure, computing device 110 may include a logical orchestration module 114. Logical orchestration module 114 may include one or more machine learning models trained to detect user interface (e.g., user interface 120, etc.) configurations and logically link to and/or recommend a multiple array of entities and services (e.g., healthcare providers/networks, treatment services, etc.), such as third-party service 116 and 118. Logical orchestration module 114 may identify entities and services with respect to user preferences/intent indicated by a user device (e.g., user device 104, etc.), and with consideration of location-based regulations/restrictions.

Logical orchestration module 114 may analyze configuration elements and metadata associated with user interface 120. The configuration elements may include structured data embedded within the user interface 120 as well as external configurations and records stored in a database/repository of logical orchestration module 114 that indicate the purpose, audience, and services for different user interfaces. Configuration information and/or metadata that may be accessed and analyzed by logical orchestration module 114 includes, but is not limited to, schema markup and structured data, API endpoints and integration data (e.g., endpoint URLs, API keys, documentation links, etc.), secure sockets layer (SSL) certificates and security configurations, configuration data gleaned from content and keyword analysis, domain-name server (DNS) records and web hosting information, and/or the like.

Additionally, logical orchestration module 114 may analyze user interface accessibility features to identify the scope/nature of a user interface. For example, a user interface, such as a healthcare website and/or the like, may implement specific accessibility features such as screen reader support, easy navigation for users with disabilities, and/or the like to accommodate users with various needs. Logical orchestration module 114 may be trained to identify that configurations that enhance accessibility (e.g., screen reader support, easy navigation for users with disabilities, etc.) might be more common in healthcare-related sites and may therefore determine that a user interface with such configurations is associated with healthcare. Alternatively, logical orchestration module 114 may parse a user interface and determine/identify outbound links and partnerships mentioned by the user interface to provide insights into any networks or platforms (e.g., healthcare networks, telehealth platforms, etc.) the user interface is associated with and automatically identify relevant services/entities (e.g., third-party services, etc.) to support the user interface via an interactive portal.

According to some aspects of this disclosure, logical orchestration module 114 may scan/parse a user interface (e.g., user interface 120, etc.) and identify the presence of social media profiles and external pages linked to the user interface. Social media profiles and external pages may be used to identify the scope/nature of a user interface and automatically identify relevant services/entities (e.g., third-party services, etc.) to support the user interface via an interactive portal. Additionally, configurations related to login mechanisms, user data encryption, user session management, regulatory compliance, and/or the like can be indicative of the scope/nature of a user interface and used to identify relevant services/entities (e.g., third-party services, etc.) to support the user interface via an interactive portal.

Figure 3:
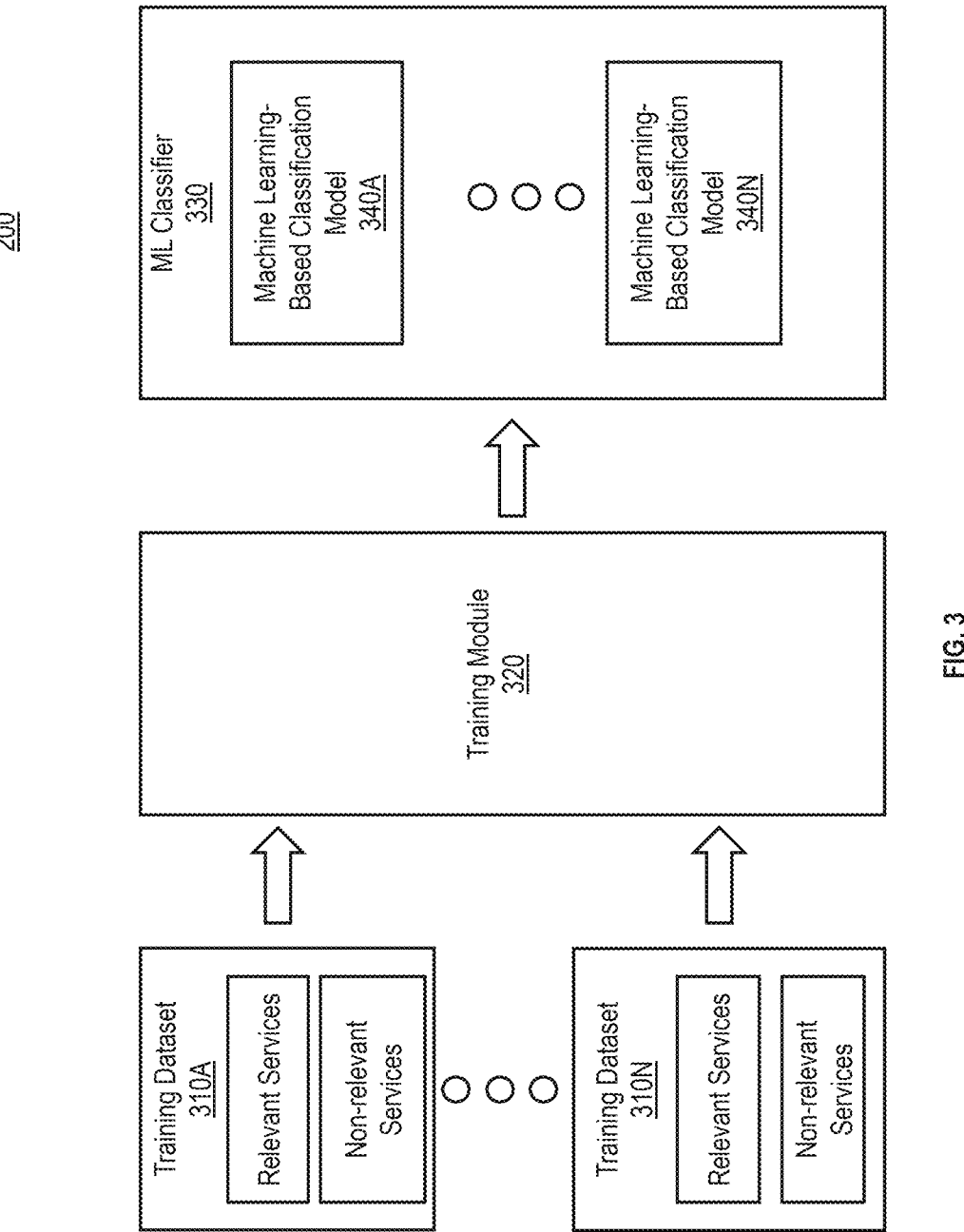
FIG. 3 shows an example system for training a logical orchestration module supporting an interactive user interface portal, according to some aspects of this disclosure.

FIG. 3 is described with reference to FIG. 1-2. As described herein, a predictive model (e.g., a machine-learning model, etc.) may be used to analyze configurations and user interactions for a user interface (e.g., user interface 120, etc.) within a host system/domain. The analysis may provide insight into various user preferences and intents for utilizing an interactive portal. For example, a website for a merchant may be analyzed to identify that the merchant website supports dental services and that a user would preferably be linked to entities (e.g., healthcare-related entities, etc.) supporting dental and related services via an interactive portal embedded in the user interface. The predictive model may dynamically recommend a personalized array of services and/or entities relevant to a user interface (e.g., healthcare services and providers, etc.) and/or user through the embedded interactive portal, taking into account user preferences, location-based regulations, and restrictions. Accordingly, the interactive portal may be logically linked to such services/entities. FIG. 3 is an example system 300 for training logical orchestration module 114 to identify services and/or entities relevant to a user interface based on the scope of the user interface, user preferences/intent, and consideration of location-based regulations/restrictions.

According to some aspects of this disclosure, system 300 may use machine learning techniques to train at least one machine learning-based classifier 330 (e.g., a software model, neural network classification layer, etc.). A machine learning-based classifier 330 may be configured by the logical orchestration module 114 based on an analysis of one or more training datasets 310A-310N. Training datasets 310A-310N may be generated from collected data including, but not limited to, information (e.g., webpage layouts, elements present on the page, various UI characteristics, etc.) about different types of user interfaces where an interactive portal could be embedded. Training datasets 310A-310N may include data (e.g., clickstreams, navigation paths, time spent on various parts of a site, etc.) describing how users interact with different host systems and embedded portals. Training datasets 310A-310N may include metrics related to how users engage with different services/entities (e.g., healthcare providers, etc.) including, but not limited to, service selection, booking rates, feedback scores, and/or the like. Training datasets 310A-310N may indicate various user interface layouts, user interaction patterns, service engagement rates, and outcomes. Training datasets 310A-310N may include regulatory information, such as details on healthcare regulations and restrictions relevant to different locations, which could impact the availability and suitability of certain services (e.g., healthcare services, etc.) and entities (e.g., healthcare providers, etc.). Training datasets 310A-310N may also incorporate location-based healthcare regulations and availability data to ensure any prediction or output (e.g., a service/entity recommendation, etc.) of a trained machine learning model complies with legal restrictions and is geographically relevant. The machine learning-based classifier 330 may be configured to classify features extracted from user interface-related data.

One or more training datasets 310A-310N may comprise labeled data indicating different URLs and/or the like of different services and entities. Feature sets may include, but are not limited to, labeled data that identifies extracted features from user interface-related data, and various data sources (e.g., third-party services 116 and 118 of FIG. 1, etc.) describing various engagements facilitated via interactive portals. The labeled data may be stored in one or more databases.

Data for logically linking user interfaces to services/entities via an interactive portal may be randomly assigned to a training dataset or a testing dataset. According to some aspects of this disclosure, the assignment of data to a training dataset or a testing dataset may not be completely random. In this case, one or more criteria may be used during the assignment, such as ensuring that similar user intents, similar communication channels, similar host domain and services pairings, similar portal interaction patterns, similar user interface interaction patterns, dissimilar user intents, dissimilar communication channels, dissimilar host domain and services pairings, dissimilar portal interaction patterns, dissimilar user interface interaction patterns, and/or the like may be used in each of the training and testing datasets. In general, any suitable method may be used to assign the data to the training or testing datasets.

The logical orchestration module 114 may train the machine learning-based classifier 330 by extracting a feature set from the labeled data according to one or more feature selection techniques. According to some aspects of this disclosure, the logical orchestration module 114 may further define the feature set obtained from the labeled data by applying one or more feature selection techniques to the labeled data in one or more training datasets 310A-310N. The logical orchestration module 114 may extract a feature set from the training datasets 310A-310N in a variety of ways. The logical orchestration module 114 may perform feature extraction multiple times, each time using a different feature-extraction technique. In some instances, the feature sets generated using the different techniques may each be used to generate different machine learning-based classification models 240. According to some aspects of this disclosure, the feature set with the highest quality metrics may be selected for use in training. The logical orchestration module 114 may use the feature set(s) to build one or more machine learning-based classification models 340A-340N that are configured to determine and/or predict user intents, communication channels, host domain and services pairings, portal interaction patterns, user interface interaction patterns, and/or the like.

According to some aspects of this disclosure, the training datasets 310A-310N and/or the labeled data may be analyzed to determine any dependencies, associations, and/or correlations between user intents, communication channels, host domain and services pairings, portal interaction patterns, user interface interaction patterns, and/or the like in the training datasets 310A-310N and/or the labeled data. The term "feature," as used herein, may refer to any characteristic of an item of data that may be used to determine whether the item of data falls within one or more specific categories. For example, the features described herein may comprise user intents, communication channels, host domain and services pairings, portal interaction patterns, user interface interaction patterns, and/or the like.

According to some aspects of this disclosure, a feature selection technique may comprise one or more feature selection rules. One or more feature selection rules may comprise determining which features in the labeled data appear over a threshold number of times in the labeled data and identifying those features that satisfy the threshold as candidate features. For example, any features that appear greater than or equal to 2 times the labeled data may be considered candidate features. Any features appearing less than 2 times may be excluded from consideration as a feature. According to some aspects of this disclosure, a single feature selection rule may be applied to select features or multiple feature selection rules may be applied to select features. According to some aspects of this disclosure, the feature selection rules may be applied in a cascading fashion, with the feature selection rules being applied in a specific order and applied to the results of the previous rule. For example, the feature selection rule may be applied to the labeled data to generate information (e.g., recommended services/entities to associate with a user interface via an interactive portal, etc.) that may be used for a user interface embedded with an interactive portal to be logically linked to a multiple array of services/entities. A final list of candidate features may be analyzed according to additional features.

According to some aspects of this disclosure, the logical orchestration module 114 may generate information (e.g., recommended services/entities to associate with a user interface via an interactive portal, etc.) that may be used for a user interface embedded with an interactive portal to be logically linked to a multiple array of services/entities based on a wrapper method. A wrapper method may be configured to use a subset of features and train the machine learning model using the subset of features. Based on the inferences that are drawn from a previous model, features may be added and/or deleted from the subset. Wrapper methods include, for example, forward feature selection, backward feature elimination, recursive feature elimination, combinations thereof, and the like. According to some aspects of this disclosure, forward feature selection may be used to identify one or more candidate user intents, communication channels, host domain and services pairings, portal interaction patterns, user interface interaction patterns, and/or the like. Forward feature selection is an iterative method that begins with no feature in the machine learning model. In each iteration, the feature that best improves the model is added until the addition of a new variable does not improve the performance of the machine learning model. According to some aspects of this disclosure, backward elimination may be used to identify one or more candidate user intents, communication channels, host domain and services pairings, portal interaction patterns, user interface interaction patterns, and/or the like. Backward elimination is an iterative method that begins with all features in the machine learning model. In each iteration, the least significant feature is removed until no improvement is observed in the removal of features. According to some aspects of this disclosure, recursive feature elimination may be used to identify one or more candidate user intents, communication channels, host domain and services pairings, portal interaction patterns, user interface interaction patterns, and/or the like. Recursive feature elimination is a greedy optimization algorithm that aims to find the best-performing feature subset. Recursive feature elimination repeatedly creates models and keeps aside the best or the worst-performing feature at each iteration. Recursive feature elimination constructs the next model with the features remaining until all the features are exhausted. Recursive feature elimination then ranks the features based on the order of their elimination.

According to some aspects of this disclosure, one or more candidate user intents, communication channels, host domain and services pairings, portal interaction patterns, user interface interaction patterns, and/or the like may be determined according to an embedded method. Embedded methods combine the qualities of filter and wrapper methods. Embedded methods include, for example, Least Absolute Shrinkage and Selection Operator (LASSO) and ridge regression which implement penalization functions to reduce overfitting. For example, LASSO regression performs L1 regularization which adds a penalty equivalent to an absolute value of the magnitude of coefficients and ridge regression performs L2 regularization which adds a penalty equivalent to the square of the magnitude of coefficients.

After logical orchestration module 114 generates a feature set(s), the logical orchestration module 114 may generate a machine learning-based classification model 340 based on the feature set(s). A machine learning-based predictive model may refer to a complex mathematical model for data classification that is generated using machine-learning techniques. For example, this machine learning-based classifier may include a map of support vectors that represent boundary features. By way of example, boundary features may be selected from, and/or represent the highest-ranked features in, a feature set.

According to some aspects of this disclosure, the logical orchestration module 114 may use the feature sets extracted from the training datasets 310A-310N and/or the labeled data to build a machine learning-based classification model 340A-340N to determine and/or predict user intents, communication channels, host domain and services pairings, portal interaction patterns, user interface interaction patterns, and/or the like. According to some aspects of this disclosure, the machine learning-based classification models 340A-340N may be combined into a single machine learning-based classification model 340 (340A-340N). Similarly, the machine learning-based classifier 330 may represent a single classifier containing a single or a plurality of machine learning-based classification models 340 and/or multiple classifiers containing a single or a plurality of machine learning-based classification models 340. According to some aspects of this disclosure, the machine learning-based classifier 330 may also include each of the training datasets 310A-310N and/or each feature set extracted from the training datasets 310A-310N and/or extracted from the labeled data. Although shown separately, logical orchestration module 114 may include the machine learning-based classifier 330.

The extracted features from the user interface and interaction data may be combined in a classification model trained using a machine learning approach such as discriminant analysis; a decision tree; a nearest neighbor (NN) algorithm (e.g., k-NN models, replicator NN models, etc.); a statistical algorithm (e.g., Bayesian networks, etc.); a clustering algorithm (e.g., k-means, mean-shift, etc.); neural networks (e.g., reservoir networks, artificial neural networks, etc.); support vector machines (SVMs); logistic regression algorithms; linear regression algorithms; Markov models or chains; a principal component analysis (PCA) (e.g., for linear models); a multi-layer perceptron (MLP) ANNs (e.g., for non-linear models); replicating reservoir networks (e.g., for non-linear models, typically for time series); random forest classification; a combination thereof and/or the like. The resulting machine learning-based classifier 330 may comprise a decision rule or a mapping that uses user interface and interaction data to determine and/or predict user intents, communication channels, host domain and services pairings, portal interaction patterns, user interface interaction patterns, and/or the like.

User interface and interaction data and/or data from various sources (e.g., third-party service 116 and 118 of FIG. 1, online and cloud-based resources, social media, etc.) describing interactions facilitated via an interactive portal embedded in various user interfaces, and the machine learning-based classifier 330 may be used to determine and/or predict user intents, communication channels, host domain and services pairings, portal interaction patterns, user interface interaction patterns, and/or the like for the test samples in the test dataset. For example, the result for each test sample may include a confidence level that corresponds to a likelihood or a probability that the corresponding test sample accurately determines and/or predicts user intents, communication channels, host domain and services pairings, portal interaction patterns, user interface interaction patterns, and/or the like. The confidence level may be a value between zero and one that represents a likelihood that the determined/predicted user intents, communication channels, host domain, and services pairings, portal interaction patterns, user interface interaction patterns, and/or the like are consistent with computed values. Multiple confidence levels may be provided for each test sample and each candidate (approximated) user intent, communication channel, host domain and services pairing, portal interaction pattern, user interface interaction pattern, and/or the like. A top-performing candidate user intent, communication channel, host domain and services pairing, portal interaction pattern, user interface interaction pattern, and/or the like may be determined by comparing the results obtained for each test sample with computed user intents, communication channels, host domain and services pairings, portal interaction patterns, user interface interaction patterns, and/or the like for each test sample. In general, the top-performing candidate user intent, communication channel, host domain and services pairing, portal interaction pattern, user interface interaction pattern, and/or the like will have results that closely match the computed user intents, communication channels, host domain and services pairings, portal interaction patterns, user interface interaction patterns, and/or the like. The top-performing candidate user intents, communication channels, host domain and services pairings, portal interaction patterns, user interface interaction patterns, and/or the like may be used to logically link to and/or recommend a multiple array of entities and services (e.g., healthcare providers/networks, treatment services, etc.) based on user interface (e.g., webpage) configurations.

Figure 4:
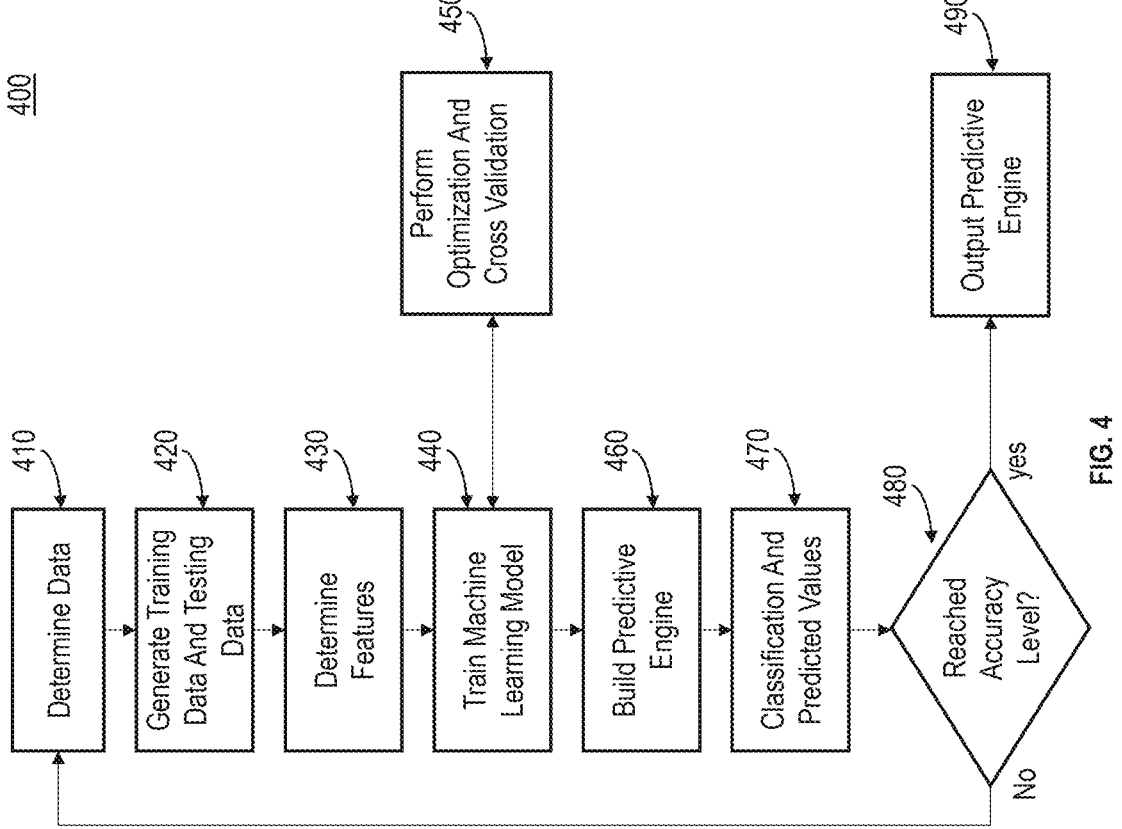
FIG. 4 shows a flowchart of an example training method for generating a machine learning classifier used with an interactive user interface portal, according to some aspects of this disclosure.

FIG. 4 is a flowchart illustrating an example training method 400. According to some aspects of this disclosure, method 400 configures machine learning classifier 430 for classification through a training process using the logical orchestration module 114. The logical orchestration module 114 can implement supervised, unsupervised, and/or semi-supervised (e.g., reinforcement-based) machine learning-based classification models 340. Method 400 shown in FIG. 4 is an example of a supervised learning method; variations of this example of training method are discussed below, however, other training methods can be analogously implemented to train unsupervised and/or semi-supervised machine learning (predictive) models. Method 400 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 4, as will be understood by a person of ordinary skill in the art.

Method 400 shall be described with reference to FIGS. 1-3. However, method 400 is not limited to the aspects of those figures.

In 410, the logical orchestration module 114 determines, receives, and/or the like, user interface and interaction data. User interface and interaction data and/or other data from various sources may be used to generate one or more datasets, each dataset associated with user intents, communication channels, host domain and services pairings, portal interaction patterns, user interface interaction patterns, and/or the like.

In 420, logical orchestration module 114 generates a training dataset and a testing dataset. According to some aspects of this disclosure, the training dataset and the testing dataset may be generated by indicating user intents, communication channels, host domain and services pairings, portal interaction patterns, user interface interaction patterns, and/or the like. According to some aspects of this disclosure, the training dataset and the testing dataset may be generated by randomly assigning user intents, communication channels, host domain and services pairings, portal interaction patterns, user interface interaction patterns, and/or the like to either the training dataset or the testing dataset. According to some aspects of this disclosure, the assignment of user interface and interaction data and/or data from various sources as training or test samples may not be completely random. According to some aspects of this disclosure, only the labeled data for a specific feature extracted from a specific user interface and interaction data and/or specific data from various sources (e.g., data indicating a preferable communication channel/type (e.g., audio vs. video, live communication vs. questionnaire, real-time feedback vs. summary reports, etc.) may be used to generate the training dataset and the testing dataset. According to some aspects of this disclosure, a majority of the labeled data extracted from user interface and interaction data and/or data from various sources may be used to generate the training dataset. For example, 75% of the labeled data for determining user intents, communication channels, host domain and services pairings, portal interaction patterns, user interface interaction patterns, and/or the like extracted from the user interface and interaction data may be used to generate the training dataset and 25% may be used to generate the testing dataset. Any method or technique may be used to create the training and testing datasets.

In 430, logical orchestration module 114 determines (e.g., extract, select, etc.) one or more features that can be used by, for example, a classifier (e.g., a software model, a classification layer of a neural network, etc.) to label features extracted from a variety of user interface and interaction data and/or data from various sources. One or more features may comprise indications of user intents, communication channels, host domain and services pairings, portal interaction patterns, user interface interaction patterns, and/or the like. According to some aspects of this disclosure, the logical orchestration module 114 may determine a set of training baseline features from the training dataset. Features of user interface and interaction data may be determined by any method.

In 440, logical orchestration module 114 trains one or more machine learning models, for example, using one or more features. According to some aspects of this disclosure, the machine learning models may be trained using supervised learning. According to some aspects of this disclosure, other machine learning techniques may be employed, including unsupervised and semi-supervised learning. The machine learning models trained in 340 may be selected based on different criteria (e.g., how close a predicted user intent, communication channel, host domain and services pairing, portal interaction pattern, user interface interaction pattern, and/or the like is to an actual user intent, communication channel, host domain and services pairing, portal interaction pattern, user interface interaction pattern, and/or the like, etc.) and/or data available in the training dataset. For example, machine learning classifiers can suffer from different degrees of bias. According to some aspects of this disclosure, more than one machine learning model can be trained.

In 450, logical orchestration module 114 optimizes, improves, and/or cross-validates trained machine learning models. For example, data for training datasets and/or testing datasets may be updated and/or revised to include more labeled data indicating different user intents, communication channels, host domain and services pairings, portal interaction patterns, user interface interaction patterns, and/ or the like.

In 460, logical orchestration module 114 selects one or more machine-learning models to build a machine-learning model (e.g., a machine-learning classifier, a predictive engine, etc.). The machine-learning model may be evaluated using the testing dataset.

In 470, logical orchestration module 114 executes the machine-learning model to analyze the testing dataset and generate classification values and/or predicted values.

In 480, logical orchestration module 114 evaluates classification values and/or predicted values output by the machine-learning model to determine whether such values have achieved the desired accuracy level. The performance of the machine-learning model may be evaluated in several ways based on a number of true positive, false positive, true negative, and/or false negative classifications of the plurality of data points indicated by the machine-learning model. For example, the false positives of the machine-learning model may refer to the number of times the machine-learning model incorrectly predicted and/or determined user intents, communication channels, host domain and services pairings, portal interaction patterns, user interface interaction patterns, and/or the like. Conversely, the false negatives of the machine-learning model may refer to the number of times the machine-learning model predicted and/or determined user intents, communication channels, host domain and services pairings, portal interaction patterns, user interface interaction patterns, and/or the like incorrectly, when in fact, the predicted and/or determined user intents, communication channels, host domain and services pairings, portal interaction patterns, user interface interaction patterns, and/or the like matches actual user intents, communication channels, host domain and services pairings, portal interaction patterns, user interface interaction patterns, and/or the like. True negatives and true positives may refer to the number of times the machine-learning model correctly predicted and/or determined user intents, communication channels, host domain and services pairings, portal interaction patterns, user interface interaction patterns, and/or the like. Related to these measurements are the concepts of recall and precision. Generally, recall refers to a ratio of true positives to a sum of true positives and false negatives, which quantifies the sensitivity of the machine-learning model. Similarly, precision refers to a ratio of true positives as a sum of true and false positives.

In 490, logical orchestration module 114 outputs the machine-learning model (and/or an output of the machine-learning model). For example, logical orchestration module 114 may output the machine-learning model when such a desired accuracy level is reached. An output of the machine-learning model may end the training phase.

According to some aspects of this disclosure, when the desired accuracy level is not reached, in 490, logical orchestration module 114 may perform a subsequent iteration of the training method 400 starting at 410 with variations such as, for example, considering a larger collection of user interface and interaction data and/or data from various sources (e.g., third-party services 116 and 118 of FIG. 1.).

FIG. 5 shows a flowchart of an example method 500 for an interactive user interface portal, according to some aspects of this disclosure. Method 500 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 5, as will be understood by a person of ordinary skill in the art. Method 400 shall be described with reference to FIGS. 1-4. However, method 500 is not limited to the aspects of those figures.

In 510, computing device 110 sends a host system of a first domain a code snippet that embeds an interactive portal into a user interface of the host system. The code snippet embeds the interactive portal into the user interface based on techniques including, but not limited to, a hypertext markup language (HTML) inline frame element, an application programming interface (API) integration, JavaScript-based widgets, reverse proxy, or cross-origin resource sharing (CORS).

According to some aspects of this disclosure, when the interactive portal is embedded in the user interface, computing device 110 may identify a visual design element of the user interface and adjust a visual design parameter of the interactive portal so that a visual design element of the interactive portal matches the visual design elements of the host system.

In 520, computing device 110 identifies location information for a user device based on an indication that the user device accessed the interactive portal. For example, computing device 110 may identify a source IP address of the user device based on an indication that the user device has logged into (or attempted to access) the user interface. Computing device 110 may include a storage module or service that maps IP addresses to locations. In a situation where the user interface supports a location-based API such as HTML5 geolocation API and/or the like, computing device 110 may use the API to request location data (e.g., GPS data, Wi-Fi data, cellular network data, IP address, etc.) from the user interface. For example, event listeners configured with the interactive portal and/or user interface may detect that the user device has logged into (or attempted to access) the user interface and inform computing device 110.

Computing device 110 may then use the API to request location data. Additionally, computing device 110 may analyze the routes taken by data packets from the user device to computing device 110, and estimate the location information based on latency and the routes.

In 530, computing device 110 identifies a service entity of a second domain based on configuration information for the user interface and the location information. The configuration information for the user interface may include, but is not limited to, a JavaScript element, a script, an API endpoint, and/or the like.

Computing device 110 may receive an indication of the service entity from a predictive model based on the configuration information for the user interface and the location information input to the predictive model. For example, the predictive model may be pre-trained to identify service entities based on user interface configurations and location-based rules for services available via user interfaces.

According to some aspects of this disclosure, computing device 110 may store or access a plurality of service profiles. A service profile may list services, functions, specialties, and/or capabilities of service entities. The predictive model may map configuration information indicative of services and/or the scope of a user interface to complementary services, functions, specialties, and/or capabilities of service entities indicated by service profiles.

In 540, computing device 110 sends user-specific content to the service entity based on interaction with the interactive portal and a cross-domain parameter of the interactive portal. The cross-domain parameter may be adjusted to enable cross-domain communication between the first and second domains. The user-specific content may include any information. For example, user-specific information may include biometric information, healthcare-related information, questionnaire-based information, video content, audio content, and/or the like.

According to some aspects of this disclosure, method 500 may further include computing device 110 detecting a change to the configuration information for the user interface. Computing device 110 may identify a different service entity of a third domain based on the changed configuration information for the user interface mapped to a service profile for the different service entity. Computing device 110 may send additional user-specific content to the different service entity based on a different interaction with the interactive portal and an update to the cross-domain parameter

EXAMPLES

Example 1: A method comprising: sending, to a host system of a first domain, a code snippet that embeds an interactive portal into a user interface of the host system; identifying a service entity of a second domain based on configuration information for the user interface mapped to a service profile for the service entity; and sending user-specific content to the service entity based on a cross-domain parameter of the interactive portal and interaction with the interactive portal.

Example 2: The method of example 1, wherein the code snippet embeds the interactive portal into the user interface via at least one of: a hypertext markup language (HTML) inline frame element, an application programming interface (API) integration, JavaScript-based widgets, reverse proxy, or cross-origin resource sharing (CORS).

Example 3: The method of examples 1-2, wherein the configuration information for the user interface comprises at least one of a JavaScript element, a script, or an API endpoint.

Example 4: The method of examples 1-3, wherein the configuration information for the user interface is accessible via an access token generated for the interactive portal.

Example 5: The method of examples 1-4, further comprising: identifying a visual design element of the user interface; and adjusting a visual design parameter of the interactive portal so that a visual design element of the interactive portal matches the visual design elements of the host system.

Example 6: The method of examples 1-5, wherein the user-specific content comprises at least one of: biometric information, healthcare-related information, questionnaire-based information, video content, or audio content.

Example 7: The method of examples 1-6, wherein the identifying the service entity of the second domain comprises receiving an indication of the service entity from a predictive model based on the based on the configuration information for the user interface and the location information input to the predictive model, wherein the predictive model is pre-trained to identify service entities based on user interface configurations and location-based rules for services available via user interfaces.

Example 8: A system comprising: one or more memories; at least one processor each coupled to at least one of the memories and configured to perform operations comprising: sending, to a host system of a first domain, a code snippet that embeds an interactive portal into a user interface of the host system; identifying a service entity of a second domain based on configuration information for the user interface mapped to a service profile for the service entity; and sending user-specific content to the service entity based on a cross-domain parameter of the interactive portal and interaction with the interactive portal.

Example 9: The system of example 8, wherein the code snippet embeds the interactive portal into the user interface via at least one of: a hypertext markup language (HTML) inline frame element, an application programming interface (API) integration, JavaScript-based widgets, reverse proxy, or cross-origin resource sharing (CORS).

Example 10: The system of examples 8-9, wherein the configuration information for the user interface comprises at least one of a JavaScript element, a script, or an API endpoint.

Example 11: The system of examples 8-10, wherein the configuration information for the user interface is accessible via an access token generated for the interactive portal.

Example 12: The system of examples 8-11, the operations further comprising: identifying a visual design element of the user interface; and adjusting a visual design parameter of the interactive portal so that a visual design element of the interactive portal matches the visual design elements of the host system.

Example 13: The system of examples 8-12, wherein the user-specific content comprises at least one of: biometric information, healthcare-related information, questionnaire-based information, video content, or audio content.

Example 14: The system of examples 8-13, wherein the identifying the service entity of the second domain comprises receiving an indication of the service entity from a predictive model based on the based on the configuration information for the user interface and the location information input to the predictive model, wherein the predictive model is pre-trained to identify service entities based on user interface configurations and location-based rules for services available via user interfaces.

Example 15: A non-transitory computer-readable medium having instructions stored thereon that, when executed by at least one computing device, cause the at least one computing device to perform operations comprising: sending, to a host system of a first domain, a code snippet that embeds an interactive portal into a user interface of the host system; identifying a service entity of a second domain based on configuration information for the user interface mapped to a service profile for the service entity; and sending user-specific content to the service entity based on a cross-domain parameter of the interactive portal and interaction with the interactive portal.

Example 16: The non-transitory computer-readable medium of example 15, wherein the code snippet embeds the interactive portal into the user interface via at least one of: a hypertext markup language (HTML) inline frame element, an application programming interface (API) integration, JavaScript-based widgets, reverse proxy, or cross-origin resource sharing (CORS).

Example 17: The non-transitory computer-readable medium of examples 15-16, wherein the configuration information for the user interface comprises at least one of a JavaScript element, a script, or an API endpoint.

Example 18: The non-transitory computer-readable medium of examples 15-17, wherein the configuration information for the user interface is accessible via an access token generated for the interactive portal.

Example 19: The non-transitory computer-readable medium of examples 15-18, the operations further comprising: identifying a visual design element of the user interface; and adjusting a visual design parameter of the interactive portal so that a visual design element of the interactive portal matches the visual design elements of the host system.

Example 20: The non-transitory computer-readable medium of examples 15-19, wherein the user-specific content comprises at least one of: biometric information, healthcare-related information, questionnaire-based information, video content, or audio content.

Example 21: A method comprising: sending, to a host system of a first domain, a code snippet that embeds an interactive portal into a user interface of the host system; and sending user-specific content to a service entity of a second domain based on interaction with the interactive portal and a cross-domain parameter of the interactive portal.

Example 22: The method of example 21, further comprising identifying the service entity based on configuration information for the user interface mapped to a service profile for the service entity.

Example 23: A method comprising: sending, to a host system of a first domain, a code snippet that embeds an interactive portal into a user interface of the host system; identifying a service entity of a second domain based on configuration information for the user interface mapped to a service profile for the service entity; sending user-specific content to the service entity based on interaction with the interactive portal and a cross-domain parameter of the interactive portal; detecting a change to the configuration information for the user interface; identifying a different service entity of a third domain based on the changed configuration information for the user interface mapped to a service profile for the different service entity; and sending additional user-specific content to the different service entity based on a different interaction with the interactive portal and an update to the cross-domain parameter.

Example 24: The method of example 23, wherein the code snippet embeds the interactive portal into the user interface via at least one of: a hypertext markup language (HTML) inline frame element, an application programming interface (API) integration, JavaScript-based widgets, reverse proxy, or cross-origin resource sharing (CORS).

Example 25: The method of examples 23-24, wherein the configuration information for the user interface comprises at least one of a JavaScript element, a script, or an API endpoint.

Example 26: The method of examples 23-25, wherein the configuration information for the user interface is accessible via an access token generated for the interactive portal.

Example 27: The method of examples 23-26, further comprising: identifying a visual design element of the user interface; and adjusting a visual design parameter of the interactive portal so that a visual design element of the interactive portal matches the visual design elements of the host system.

Example 28: The method of examples 23-27, wherein the user-specific content and the additional user-specific content comprise at least one of: biometric information, healthcare-related information, questionnaire-based information, video content, or audio content.

Example 29: The method of examples 23-28, wherein the detecting the change to the configuration information for the user interface comprises receiving an indication of the change from an event listener configured via the code snippet to identify configuration changes.

Example 30: A system comprising: one or more memories; at least one processor each coupled to at least one of the memories and configured to perform operations comprising: sending, to a host system of a first domain, a code snippet that embeds an interactive portal into a user interface of the host system; identifying a service entity of a second domain based on configuration information for the user interface mapped to a service profile for the service entity; sending user-specific content to the service entity based on interaction with the interactive portal and a cross-domain parameter of the interactive portal; detecting a change to the configuration information for the user interface; identifying a different service entity of a third domain based on the changed configuration information for the user interface mapped to a service profile for the different service entity; and sending additional user-specific content to the different service entity based on a different interaction with the interactive portal and an update to the cross-domain parameter.

Example 31: The system of example 30, wherein the code snippet embeds the interactive portal into the user interface via at least one of: a hypertext markup language (HTML) inline frame element, an application programming interface (API) integration, JavaScript-based widgets, reverse proxy, or cross-origin resource sharing (CORS).

Example 32: The system of examples 30-31, wherein the configuration information for the user interface comprises at least one of a JavaScript element, a script, or an API endpoint.

Example 33: The system of examples 30-32, wherein the configuration information for the user interface is accessible via an access token generated for the interactive portal.

Example 34: The system of examples 30-33, the operations further comprising: identifying a visual design element of the user interface; and adjusting a visual design parameter of the interactive portal so that a visual design element of the interactive portal matches the visual design elements of the host system.

Example 35: The system of examples 30-34, wherein the user-specific content and the additional user-specific content comprise at least one of: biometric information, healthcare-related information, questionnaire-based information, video content, or audio content.

Example 36: The system of examples 30-35, wherein the detecting the change to the configuration information for the user interface comprises receiving an indication of the change from an event listener configured via the code snippet to identify configuration changes.

Example 37: A non-transitory computer-readable medium having instructions stored thereon that, when executed by at least one computing device, cause the at least one computing device to perform operations comprising: sending, to a host system of a first domain, a code snippet that embeds an interactive portal into a user interface of the host system; identifying a service entity of a second domain based on configuration information for the user interface mapped to a service profile for the service entity; sending user-specific content to the service entity based on interaction with the interactive portal and a cross-domain parameter of the interactive portal; detecting a change to the configuration information for the user interface; identifying a different service entity of a third domain based on the changed configuration information for the user interface mapped to a service profile for the different service entity; and sending additional user-specific content to the different service entity based on a different interaction with the interactive portal and an update to the cross-domain parameter.

Example 38: The non-transitory computer-readable medium of example 37, wherein the code snippet embeds the interactive portal into the user interface via at least one of: a hypertext markup language (HTML) inline frame element, an application programming interface (API) integration, JavaScript-based widgets, reverse proxy, or cross-origin resource sharing (CORS).

Example 39: The non-transitory computer-readable medium of examples 37-38, wherein the configuration information for the user interface comprises at least one of a JavaScript element, a script, or an API endpoint.

Example 40: The non-transitory computer-readable medium of examples 37-39, wherein the configuration information for the user interface is accessible via an access token generated for the interactive portal.

Example 41: The non-transitory computer-readable medium of examples 37-40, the operations further comprising: identifying a visual design element of the user interface; and adjusting a visual design parameter of the interactive portal so that a visual design element of the interactive portal matches the visual design elements of the host system.

Example 42: The non-transitory computer-readable medium of examples 37-41, wherein the user-specific content and the additional user-specific content comprise at least one of: biometric information, healthcare-related information, questionnaire-based information, video content, or audio content.

Example 43: The non-transitory computer-readable medium of examples 37-42, wherein the detecting the change to the configuration information for the user interface comprises receiving an indication of the change from an event listener configured via the code snippet to identify configuration changes.

Figure 6:
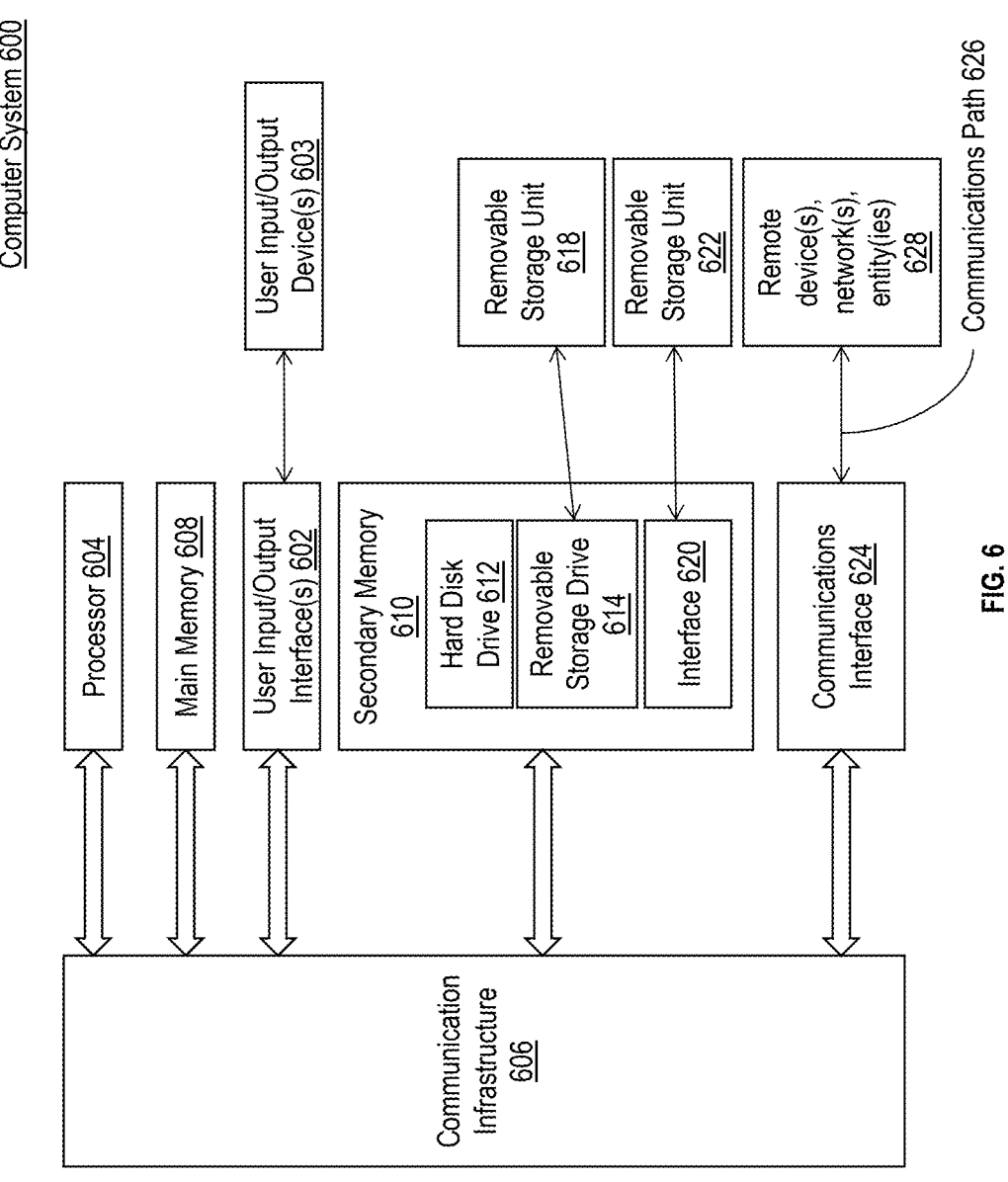
FIG. 6 is an example computer system useful for implementing various aspects of this disclosure.

Various embodiments may be implemented, for example, using one or more well-known computer systems, such as computer system 600 shown in FIG. 6. For example, user device 104, computing device 110, third-party services 116 and 118, and/or any other device/component described herein may be implemented using combinations or sub-combinations of computer system 600. Also or alternatively, one or more computer systems 600 may be used, for example, to implement any of the embodiments discussed herein, as well as combinations and sub-combinations thereof.

Computer system 600 may include one or more processors (also called central processing units, or CPUs), such as a processor 604. Processor 604 may be connected to a communication infrastructure or bus 606.

Computer system 600 may also include user input/output device(s) 603, such as monitors, keyboards, pointing devices, etc., which may communicate with communication infrastructure 606 through user input/output interface(s) 602.

One or more of processors 604 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 600 may also include a main or primary memory 608, such as random access memory (RAM). Main memory 608 may include one or more levels of cache. Main memory 608 may have stored therein control logic (i.e., computer software) and/or data.

Computer system 600 may also include one or more secondary storage devices or memory 610. Secondary memory 610 may include, for example, a hard disk drive 612 and/or a removable storage device or drive 614. Removable storage drive 614 may be a floppy disk drive, a magnetic tape drive, a compact disk drive, an optical storage device, a tape backup device, and/or any other storage device/drive.

Removable storage drive 614 may interact with a removable storage unit 618. Removable storage unit 618 may include a computer-usable or readable storage device having stored thereon computer software (control logic) and/or data. Removable storage unit 618 may be a floppy disk, magnetic tape, compact disk, DVD, optical storage disk, and/or any other computer data storage device. Removable storage drive 614 may read from and/or write to removable storage unit 618.

Secondary memory 610 may include other means, devices, components, instrumentalities, or other approaches for allowing computer programs and/or other instructions and/or data to be accessed by computer system 600. Such means, devices, components, instrumentalities, or other approaches may include, for example, a removable storage unit 622 and an interface 620. Examples of the removable storage unit 622 and the interface 620 may include a program cartridge and cartridge interface (such as that found in video game devices), a removable memory chip (such as an EPROM or PROM) and associated socket, a memory stick and USB or other port, a memory card and associated memory card slot, and/or any other removable storage unit and associated interface.

Computer system 600 may further include a communication or network interface 624. Communication interface 624 may enable computer system 600 to communicate and interact with any combination of external devices, external networks, external entities, etc. (individually and collectively referenced by reference number 628). For example, communication interface 624 may allow computer system 600 to communicate with external or remote devices 628 over communications path 626, which may be wired and/or wireless (or a combination thereof), and which may include any combination of LANs, WANs, the Internet, etc. Control logic and/or data may be transmitted to and from computer system 600 via communication path 626.

Computer system 600 may also be any of a personal digital assistant (PDA), desktop workstation, laptop or notebook computer, netbook, tablet, smartphone, smartwatch or other wearable, appliance, part of the Internet-of-Things, and/or embedded system, to name a few non-limiting examples, or any combination thereof.

Computer system 600 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 600 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats, or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 600, main memory 608, secondary memory 610, and removable storage units 618 and 622, as well as tangible articles of manufacture embodying any combination of the foregoing. Such control logic, when executed by one or more data processing devices (such as computer system 600 or processor(s) 604), may cause such data processing devices to operate as described herein.

Based on the teachings contained in this disclosure, it will be apparent to persons skilled in the relevant art(s) how to make and use embodiments of this disclosure using data processing devices, computer systems, and/or computer architectures other than that shown in FIG. 6. In particular, embodiments can operate with software, hardware, and/or operating system implementations other than those described herein.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. Additionally, some embodiments can be described using the expressions "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents.

What is claimed is:

1. A computer-implemented method for an interactive user interface portal, comprising:

sending, to a host system of a first domain, a code snippet that embeds an interactive portal into a user interface of the host system;

identifying, by at least one computer processor, location information for a user device based on an indication that the user device accessed the interactive portal;

adjusting a visual design parameter of the interactive portal so that a visual design element of the interactive portal matches a visual design element of the user interface;

identifying a service entity of a second domain that provides a service via the user interface based on configuration information for the user interface and the location information;

sending first user-specific content to the service entity of the second domain based on a first interaction with the interactive portal and a cross-domain parameter of the interactive portal;

detecting, via an event listener configured via the code snippet to identify configuration changes, a change to the configuration information for the user interface that implements a new service via the user interface;

identifying a service entity of a third domain that provides the new service based on the detected change to the configuration information for the user interface being mapped to a service profile for the service entity of the third domain, wherein the service entity of the third domain is different from the service entity of the second domain; and sending second user-specific content to the service entity of the third domain based on a second interaction with the interactive portal and an update to the cross-domain parameter.

2. The computer-implemented method of claim 1, wherein the code snippet embeds the interactive portal into the user interface via at least one of a hypertext markup language (HTML) inline frame element, an application programming interface (API) integration, JavaScript- based widgets, reverse proxy, or cross-origin resource sharing (CORS).

3. The computer-implemented method of claim 1, wherein the configuration information for the user interface comprises at least one of a JavaScript element, a script, or an application programming interface (API) endpoint.

4. The computer-implemented method of claim 1, wherein at least one of the first user-specific content or the second user-specific content comprises at least one of bio-metric information, healthcare-related information, questionnaire-based information, video content, or audio content.

5. The computer-implemented method of claim 1, wherein the identifying the service entity of the second domain comprises receiving an indication of the service entity from a predictive model based on the configuration information for the user interface and the location information input to the predictive model, wherein the predictive model is pre-trained to identify service entities based on user interface configurations and location-based rules for ser-vices available via user interfaces.

6. The computer-implemented method of claim 1, wherein identifying a service entity of the second domain is based on configuration information for the user interface mapped to a service profile for the service entity of the second domain, wherein the service profile comprises ser-vices, functions, specialties, or capabilities of the service entity of the second domain.

7. A system for an interactive user interface portal, comprising:

one or more memories; and at least one processor each coupled to at least one of the memories and configured to perform operations com-prising:

sending, to a host system of a first domain, a code snippet that embeds an interactive portal into a user interface of the host system;

identifying location information for a user device based on an indication that the user device accessed the interactive portal;

adjusting a visual design parameter of the interactive portal so that a visual design element of the interactive portal matches a visual design element of the user interface;

identifying a service entity of a second domain that provides a service via the user interface based on configuration information for the user interface and the location information;

sending first user-specific content to the service entity of the second domain based on a first interaction with the interactive portal and a cross-domain parameter of the interactive portal;

detecting, via an event listener configured via the code snippet to identify configuration changes, a change to the configuration information for the user interface that implements a new service via the user interface;

identifying a service entity of a third domain that provides the new service based on the detected change to the configuration information for the user interface being mapped to a service profile for the service entity of the third domain, wherein the service entity of the third domain is different from the service entity of the second domain; and sending second user-specific content to the service entity of the third domain based on a second interaction with the interactive portal and an update to the cross-domain parameter.

8. The system of claim 7, wherein the code snippet embeds the interactive portal into the user interface via at least one of a hypertext markup language (HTML) inline frame element, an application programming interface (API) integration, JavaScript-based widgets, reverse proxy, or cross-origin resource sharing (CORS).

9. The system of claim 7, wherein the configuration information for the user interface comprises at least one of a JavaScript element, a script, or an application program-ming interface (API) endpoint.

10. The system of claim 7, wherein at least one of the first user- specific content or the second user-specific content comprises at least one of biometric information, healthcare-related information, questionnaire-based information, video content, or audio content.

11. The system of claim 7, wherein the identifying the service entity of the second domain comprises receiving an indication of the service entity from a predictive model based on the configuration information for the user interface and the location information input to the predictive model, wherein the predictive model is pre-trained to identify service entities based on user interface configurations and location-based rules for services available via user inter-faces.

12. A non-transitory computer-readable medium having instructions stored thereon that, when executed by at least one computing device, cause the at least one computing device to perform operations comprising:

sending, to a host system of a first domain, a code snippet that embeds an interactive portal into a user interface of the host system;

identifying location information for a user device based on an indication that the user device accessed the interactive portal;

adjusting a visual design parameter of the interactive portal so that a visual design element of the interactive portal matches a visual design element of the user interface;

identifying a service entity of a second domain that provides a service via the user interface based on configuration information for the user interface and the location information;

sending first user-specific content to the service entity of the second domain based on a first interaction with the interactive portal and a cross-domain parameter of the interactive portal;

detecting, via an event listener configured via the code snippet to identify configuration changes, a change to the configuration information for the user interface that implements a new service via the user interface;

identifying a service entity of a third domain that provides the new service based on the detected change to the configuration information for the user interface being mapped to a service profile for the service entity of the third domain, wherein the service entity of the third domain is different from the service entity of the second domain; and sending second user-specific content to the service entity of the third domain based on a second interaction with the interactive portal and an update to the cross-domain parameter.

13. The non-transitory computer-readable medium of claim 12, wherein the code snippet embeds the interactive portal into the user interface via at least one of a hypertext markup language (HTML) inline frame element, an application programming interface (API) integration, JavaScript-based widgets, reverse proxy, or cross-origin resource sharing (CORS).

14. The non-transitory computer-readable medium of claim 12, wherein the configuration information for the user interface comprises at least one of a JavaScript element, a script, or an API endpoint.

15. The non-transitory computer-readable medium of claim 12, wherein at least one of the first user-specific content or the second user-specific content comprises at least one of: biometric information, healthcare-related information, questionnaire-based information, video content, or audio content.

16. The non-transitory computer-readable medium of claim 12, wherein the identifying the service entity of the second domain comprises receiving an indication of the service entity from a predictive model based on the configuration information for the user interface and the location information input to the predictive model, wherein the predictive model is pre-trained to identify service entities based on user interface configurations and location-based rules for services available via user interfaces.

\* \* \* \* \*